(12) United States Patent
Yamashita

(10) Patent No.: US 8,620,401 B2
(45) Date of Patent: Dec. 31, 2013

(54) BIOLOGICAL SIGNAL DETECTION ELECTRODE AND BIOLOGICAL SIGNAL DETECTION APPARATUS

(75) Inventor: Shiko Yamashita, Tokyo (JP)

(73) Assignee: Sony Corporation, Tokyo (JP)

( * ) Notice: Subject to any disclaimer, the term of this patent is extended or adjusted under 35 U.S.C. 154(b) by 172 days.

(21) Appl. No.: 13/157,961

(22) Filed: Jun. 10, 2011

(65) Prior Publication Data

US 2011/0315548 A1 Dec. 29, 2011

(30) Foreign Application Priority Data

Jun. 28, 2010 (JP) ................................. 2010-146744

(51) Int. Cl.
*A61B 5/0478* (2006.01)

(52) U.S. Cl.
USPC ........................................... 600/383; 600/397

(58) Field of Classification Search
USPC ......................................... 600/383, 397, 544
See application file for complete search history.

(56) References Cited

U.S. PATENT DOCUMENTS

| | | | | |
|---|---|---|---|---|
| 2,555,037 A | * | 5/1951 | Jensen | 600/397 |
| 3,508,541 A | * | 4/1970 | Westbrook et al. | 600/383 |
| 3,896,790 A | * | 7/1975 | Dikmen | 600/383 |
| 3,989,036 A | * | 11/1976 | Sasamori | 600/396 |
| 5,289,822 A | | 3/1994 | Highe et al. | |
| 5,330,527 A | | 7/1994 | Montecalvo et al. | |
| 6,067,464 A | * | 5/2000 | Musha | 600/383 |
| 6,510,333 B1 | * | 1/2003 | Licata et al. | 600/383 |
| 7,930,013 B2 | * | 4/2011 | Ponton | 600/383 |

FOREIGN PATENT DOCUMENTS

| | | |
|---|---|---|
| EP | 1767147 | 3/2007 |
| JP | 10-165386 | 6/1998 |
| JP | 2006-006666 | 1/2006 |
| JP | 2006-34429 | 2/2006 |

OTHER PUBLICATIONS

European Patent Office, Extended European Search Report issued in connection with European Patent Application No. 11004727.1, dated Nov. 2, 2011. (8 pages).

European Patent Office, Communication pursuant to Article 94(3) EPC issued in connection with European Patent Application No. 11 004 727.1, dated Jul. 8, 2013. (7 pages).

* cited by examiner

*Primary Examiner* — Lee S Cohen
(74) *Attorney, Agent, or Firm* — K&L Gates LLP

(57) ABSTRACT

A biological signal detection electrode includes an electrode element and a plurality of drought-resistant electrolytic solution soaking parts. The electrode element is made of a conductive material and has a surface. The plurality of drought-resistant electrolytic solution soaking parts are placed at predetermined intervals on the surface of the electrode element, are formed to have a thickness that allows contact with a scalp without hair being sandwiched between the electrode element and the scalp, and are soaked in a drought-resistant electrolytic solution including a drought-resistant liquid and a conductive liquid.

6 Claims, 8 Drawing Sheets

1

1

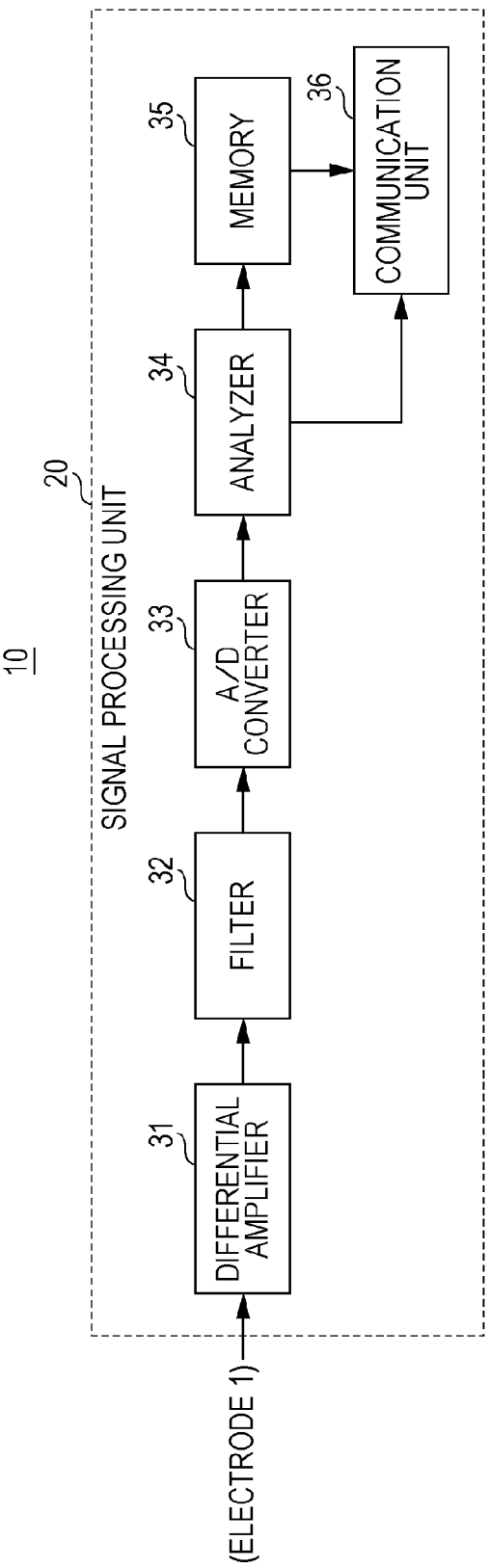

BIOLOGICAL SIGNAL DETECTION ELECTRODE AND BIOLOGICAL SIGNAL DETECTION APPARATUS

CROSS REFERENCES TO RELATED APPLICATIONS

The present application claims priority to Japanese Priority Patent Application JP 2010-146744 filed in the Japan Patent Office on Jun. 28, 2010, the entire contents of which are hereby incorporated by reference.

BACKGROUND

The present application relates to a biological signal detection electrode and a biological signal detection apparatus that are preferably applied when, for example, brain waves are obtained as electronic signals.

There is a related-art apparatus obtaining brain waves from many electrodes that are disposed on a headgear etc. and in contact with the scalp of a test subject wearing the headgear.

The electrodes of this apparatus are attached to the scalp using an electrically conductive paste because there are differences in the presence of hair or the head shape among individuals.

Accordingly, this apparatus imposes troublesome work such as attachment of many electrodes to the scalp as well as washing of hair to remove the paste.

Japanese Unexamined Patent Application Publications No. 2006-6666 and No. 2006-34429, etc. propose an electrode in which an elastic member soaked in a conductive liquid of physiological saline or a mixture of physiological saline and alcohol is closely disposed at the end of a conductive member, the physiological saline or the mixture is seeped when the elastic member is pushed against the scalp, and the conductive member is electrically connected to the scalp via the physiological saline or the mixture.

Japanese Unexamined Patent Application Publication No. 10-165386 etc. propose an electrode in which a felt piece including a bundle of bonded felt bars with round tips containing a conductive liquid is brought into contact with the scalp to obtain brain wave signals.

SUMMARY

Since the electrodes proposed by Japanese Unexamined Patent Application Publications No. 2006-6666, No. 2006-34429, and No. 10-165386 use physiological saline or a mixture of physiological saline and alcohol as a conductive liquid, there is a problem in that the conductive liquid easily evaporates and the electrical connection between the conductive member and the scalp is degraded by the evaporation of the conductive liquid in a long-term measurement, thereby disabling the correct measurement of brain wave signals.

In the electrodes proposed by Japanese Unexamined Patent Application Publications No. 2006-6666 and No. 2006-34429, since the contact area between the conductive member and the scalp is, for example, approximately 19 $mm^2$ to approximately 314 $mm^2$ to improve the electrical connection between the conductive member and the scalp, the conductive member is pushed against the scalp via hair. Accordingly, measurement becomes unstable because the elastic member does not make physical contact with the scalp.

Since the electrode proposed by Japanese Unexamined Patent Application Publication No. 10-165386 includes a bundle of felt bars which have round tips, when the felt piece is pushed against the scalp, the possibility that the tips of the felt bars make direct contact with the scalp increases. However, when, for example, the amount of hair is large, the felt piece may not make physical contact with the scalp head because hair may be sandwiched therebetween, and measurement becomes unstable.

It is desirable to provide a biological signal detection electrode and a biological signal detection apparatus that stably measure biological signals for a long time.

According to an embodiment, there is provided a biological signal detection electrode including an electrode element that is made of a conductive material and has a surface and a plurality of drought-resistant electrolytic solution soaking parts that are placed at predetermined intervals on the surface of the electrode element, are formed to have a thickness that allows contact with a scalp without hair being sandwiched between the electrode element and the scalp, and are soaked in a drought-resistant electrolytic solution including a drought-resistant liquid and a conductive liquid.

According to an embodiment, there is provided a biological signal detection apparatus that includes an electrode having an electrode element made of a conductive material, the electrode element having a surface, and a plurality of drought-resistant electrolytic solution soaking parts that are placed at predetermined intervals on the surface of the electrode element, are formed to have a thickness allowing contact with a scalp without hair being sandwiched between the electrode element and the scalp, and are soaked in a drought-resistant electrolytic solution including a drought-resistant liquid and a conductive liquid, and pushing unit pushing the electrode with a predetermined pushing force against a scalp of a wearer.

According to the embodiment, when the end of the drought-resistant electrolytic solution soaking part makes contact with the scalp, even if hair is present therebetween, the end easily makes contact with the scalp and the drought-resistant liquid suppresses the evaporation of conductive liquid, thereby enabling stable measurement of biological signals for a long time.

BRIEF DESCRIPTION OF THE FIGURES

FIG. 9 is a schematic diagram showing the configuration of a signal processing unit.

Additional features and advantages are described herein, and will be apparent from the following Detailed Description and the figures.

DETAILED DESCRIPTION

Embodiments of the present application will be described below in detail with reference to the drawings.

Embodiments of the present application will be described in the order shown below.
1. Embodiment
2. Other Embodiments

1. Embodiment

1. Configuration of an Electrode

Figure 1:
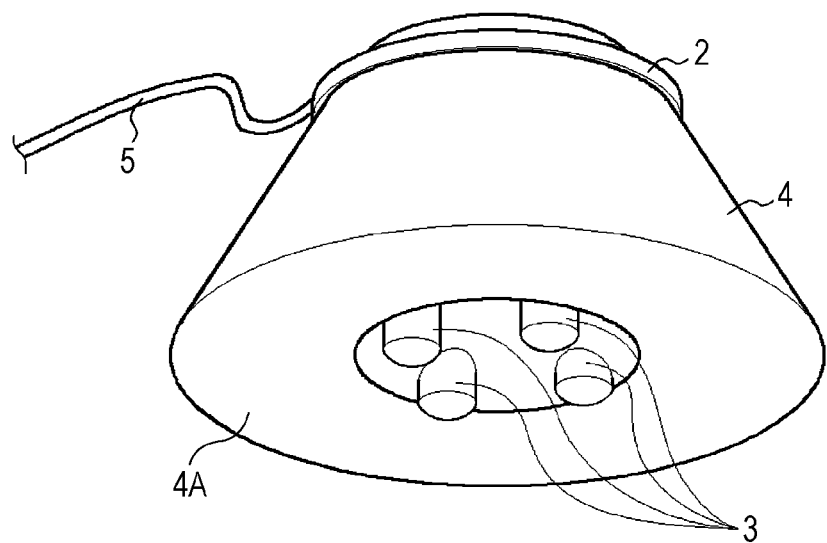
FIG. 1 is a schematic diagram showing the configuration of an electrode.

FIG. 1 shows an electrode 1 according to an embodiment. The electrode 1 includes an electrode element 2, a drought-resistant electrolytic solution soaking part 3, a support part 4, and a conducting wire 5.

The electrode element 2 is made of a highly-conductive material such as gold and formed in a substantially circular shape, and the conducting wire 5 is connected to a predetermined position on the side of the circular shape.

Figure 2:
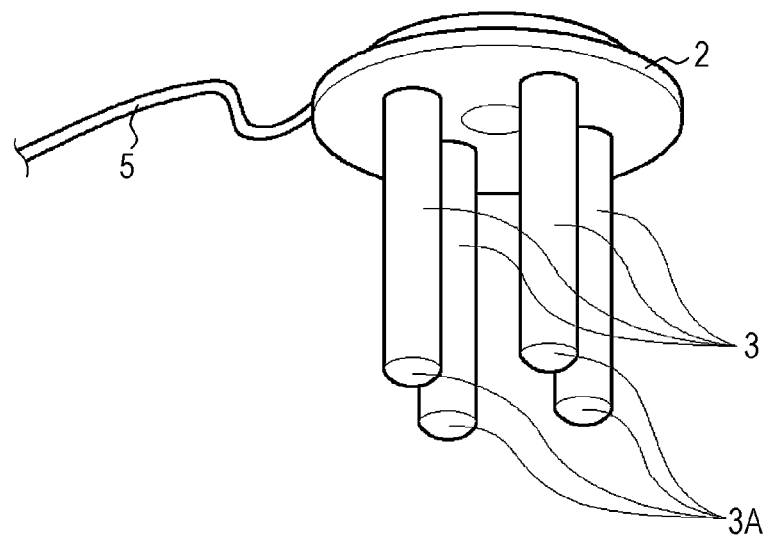
FIG. 2 is a schematic diagram showing the configuration of the electrode from which a support part has been removed.
Figure 3:
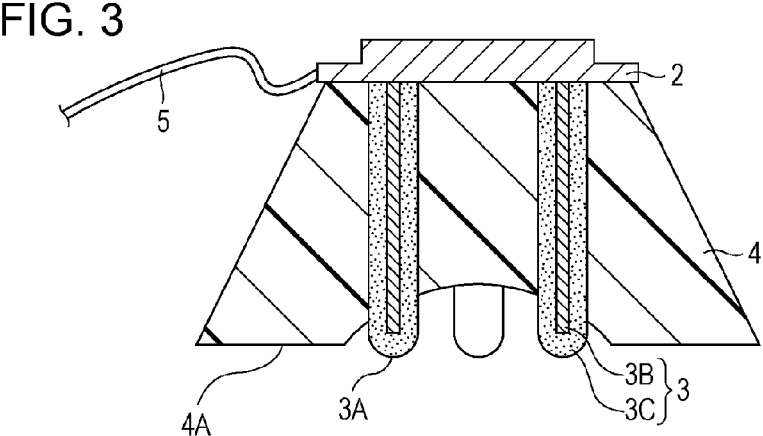
FIG. 3 is a sectional view showing the electrode.

As shown in FIGS. 2 and 3, the drought-resistant electrolytic solution soaking part 3 is formed in a substantially cylindrical shape with a diameter of approximately 2 mm and a length of approximately 10 mm, and an end 3A opposite to the side of the electrode element 2 is formed in a substantially hemispherical shape. In the drought-resistant electrolytic solution soaking part 3, a textile piece 3C, which is made of absorbent cotton etc. is wound around the entire side including the end 3A of a core 3B, which is made of paper, wood, plastic, etc.

The end of drought-resistant electrolytic solution soaking part 3 that is not covered with the textile piece 3C is bonded to one side of the electrode element 2 with a conductive adhesive etc.

Four drought-resistant electrolytic solution soaking parts 3 are attached to the one side of the electrode element 2; of the drought-resistant electrolytic solution soaking parts 3, adjacent ones are spaced apart by a distance larger than their diameter with the four drought-resistant electrolytic solution soaking parts 3 placed in the four corners of a square with a predetermined size.

The textile piece 3C of the drought-resistant electrolytic solution soaking part 3 is soaked in the drought-resistant electrolytic solution that is created by mixing conductive physiological saline (containing approximately 1% sodium chloride) and glycerin, which is highly water-retentive, at the rate of approximately 3 to 7.

Accordingly, when the end 3A of the drought-resistant electrolytic solution soaking part 3 makes contact with the scalp of the test subject, the drought-resistant electrolytic solution transfers brain wave signals to the electrode element 2 via physiological saline and glycerin suppresses the evaporation of physiological saline.

This enables the drought-resistant electrolytic solution soaking part 3 soaked in the drought-resistant electrolytic solution to stably transfer brain wave signals to the electrode element 2 without the drought-resistant electrolytic solution drying even in long-term measurement.

The support part 4 is made of an elastic material such as polyurethane and formed in a substantially truncated-conical shape and the height (for example, 8 mm) is slightly longer than the length of the drought-resistant electrolytic solution soaking part 3, the area of the upper surface is approximately the same as the area of the electrode element 2, and the area of the bottom surface 4A is larger than the area of the upper surface.

Four through holes with a diameter approximately the same as that of the drought-resistant electrolytic solution soaking part 3 are disposed in the support part 4 between the upper surface and the bottom surface 4A with the positions of the through holes corresponding to those of the drought-resistant electrolytic solution soaking parts 3. Accordingly, when the drought-resistant electrolytic solution soaking parts 3 are inserted into the through holes of the support part 4 in the electrode 1, the ends 3A of the drought-resistant electrolytic solution soaking parts 3 project from the bottom surface 4A of the support part 4.

A round concave portion is formed in a predetermined range including the through holes with respect to the center of the bottom surface 4A in the support part 4. Accordingly, when the electrode 1 makes contact with the scalp, the concave portion of the bottom surface 4A does not make contact with the scalp and the outer section of the bottom surface 4A other than the concave portion makes contact with the scalp or hair.

When the electrode 1 is used to measure the brain waves of the test subject, the ends 3A of the drought-resistant electrolytic solution soaking parts 3 are first brought into contact with the scalp of the test subject and then brain wave signals are obtained through the drought-resistant electrolytic solution soaking parts 3, the electrode element 2, and the conducting wire 5.

Accordingly, in the electrode 1, it may be necessary to bring the ends 3A of the drought-resistant electrolytic solution soaking parts 3 into contact with the scalp of the test subject regardless of differences in the presence of hair or the head shape among individuals.

Figure 4A:
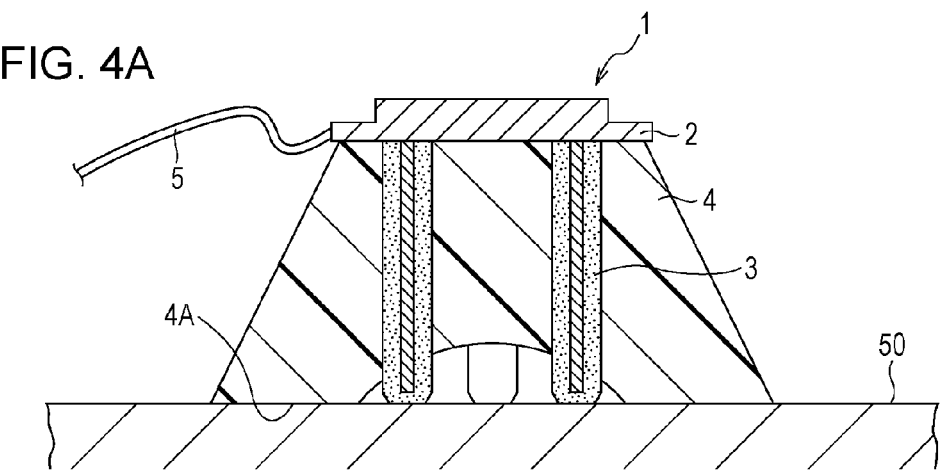
FIGS. 4A and 4B are schematic diagrams showing the electrode in contact with a scalp.

When the electrode 1 is pushed against a scalp 50 having no hair with a predetermined pushing force as shown in FIG. 4A, the ends 3A of the drought-resistant electrolytic solution soaking parts 3 make contact with the scalp 50.

Although the drought-resistant electrolytic solution soaking parts 3 are slightly longer than the height of the support part 4 in the electrode 1, the bottom surface 4A of the support part 4 makes contact with the scalp 50 because the ends 3A shrink due to the pushing force. Since the ends 3A of the drought-resistant electrolytic solution soaking parts 3 are round, pushing the electrode 1 against the scalp 50 with the predetermined pushing force gives little pain to the wearer.

Accordingly, when the electrode 1 is used for the scalp 50 that has no hair, the ends 3A of the drought-resistant electrolytic solution soaking parts 3 are kept in contact with the scalp 50 by the predetermined pushing force.

In addition, the electrode 1 makes contact with the scalp 50 in a wider area since the bottom surface 4A of the support part 4 makes contact with the scalp 50, so the state where the end 3A makes contact with the scalp 50 is kept more stable.

Figure 4B:
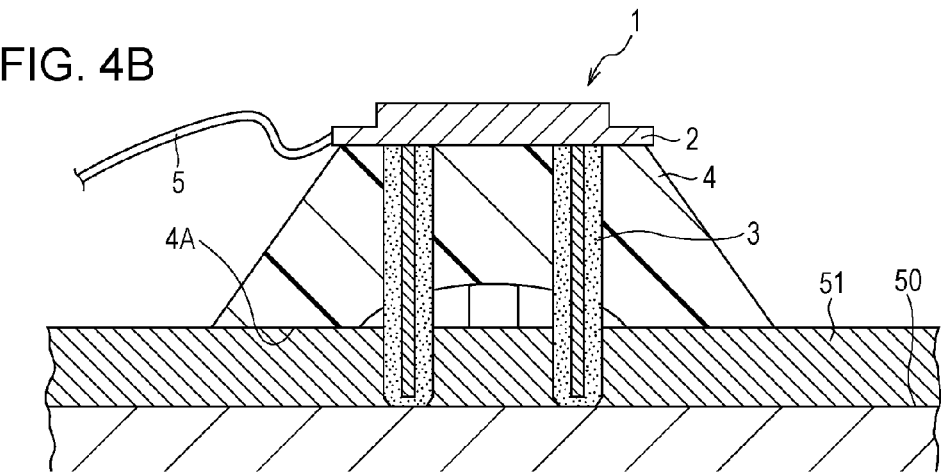

On the other hand, when the electrode 1 is used for the scalp 50 that has hair 51 as shown in FIG. 4B, if the electrode 1 is pushed against the scalp 50 with a predetermined pushing force, the hair 51 is sandwiched between the bottom surface 4A of the support part 4 and the scalp 50 and the support part 4 shrinks in the height direction by the amount corresponding to the thickness of the hair 51 sandwiched.

Since the support part 4 shrinks in the height direction in the electrode 1, the amount of projection of the drought-resistant electrolytic solution soaking part 3 from the bottom surface 4A of the support part 4 increases by the distance between the bottom surface 4A of the support part 4 and the scalp 50 and the end 3A of the drought-resistant electrolytic solution soaking part 3 makes contact with the scalp 50.

Since the drought-resistant electrolytic solution soaking part 3 has a diameter of approximately 2 mm and the end 3A is formed in a substantially hemispherical shape, when the electrode 1 is pushed against the scalp 50 with a predetermined pushing force, the end 3A makes contact with the scalp 50 without the hair 51 being sandwiched therebetween.

Accordingly, when the electrode 1 is used for the scalp 50 that has the hair 51, the support part 4 shrinks due to a predetermined pushing force in the thickness direction by the thickness of the hair 51 sandwiched between the bottom surface 4A of the support part 4 and the scalp 50. Since the drought-resistant electrolytic solution soaking part 3 projects from the support part 4 by the thickness, the state where the end 3A makes contact with the scalp 50 is kept in the electrode 1.

Since the bottom surface 4A of the support part 4 is shrunk and deformed because the hair 51 is sandwiched at this time, the electrode 1 pushes the hair 51 against the scalp 50 by a restoring force and the state where the end 3A makes contact with the scalp 50 is kept more stable.

2. Measurement Result

Figure 5:
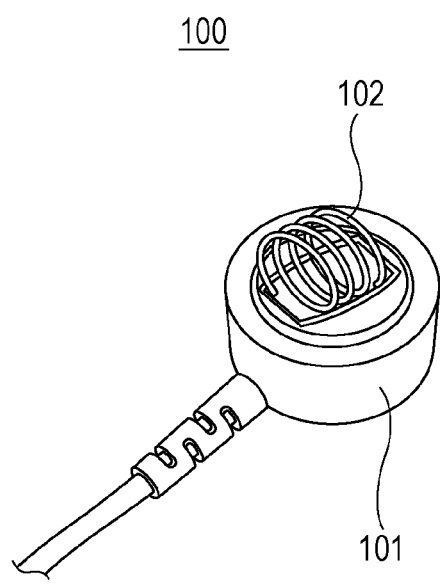
FIG. 5 is a schematic view showing a coil electrode.

Next, the measurement results of the impedances of the electrode 1, a commercially available coil electrode 100 for measurement of brain waves shown in FIG. 5, and an electrode (referred to below as the reference electrode) used as the reference during measurement of brain waves, described later.

In the coil electrode 100, a circular electrode chip 102 (AP-P110m manufactured by DIGITEX LAB.) is attached to the electrode surface of a main body 101 (AP-C300 manufactured by DIGITEX LAB.) including a conducting wire, using conductive double-faced tape.

The impedances were measured using the impedance check mode of the software that comes with Polymate II (AP216 manufactured by DIGITEX LAB.).

These impedances were measured by placing the electrode 1 and the coil electrode 100 near the vertex of the wearer, placing the reference electrode at the wearer' ear lobule, and using another electrode placed at the wearer' ear lobule as a reference electrode in this measurement.

Figure 6:
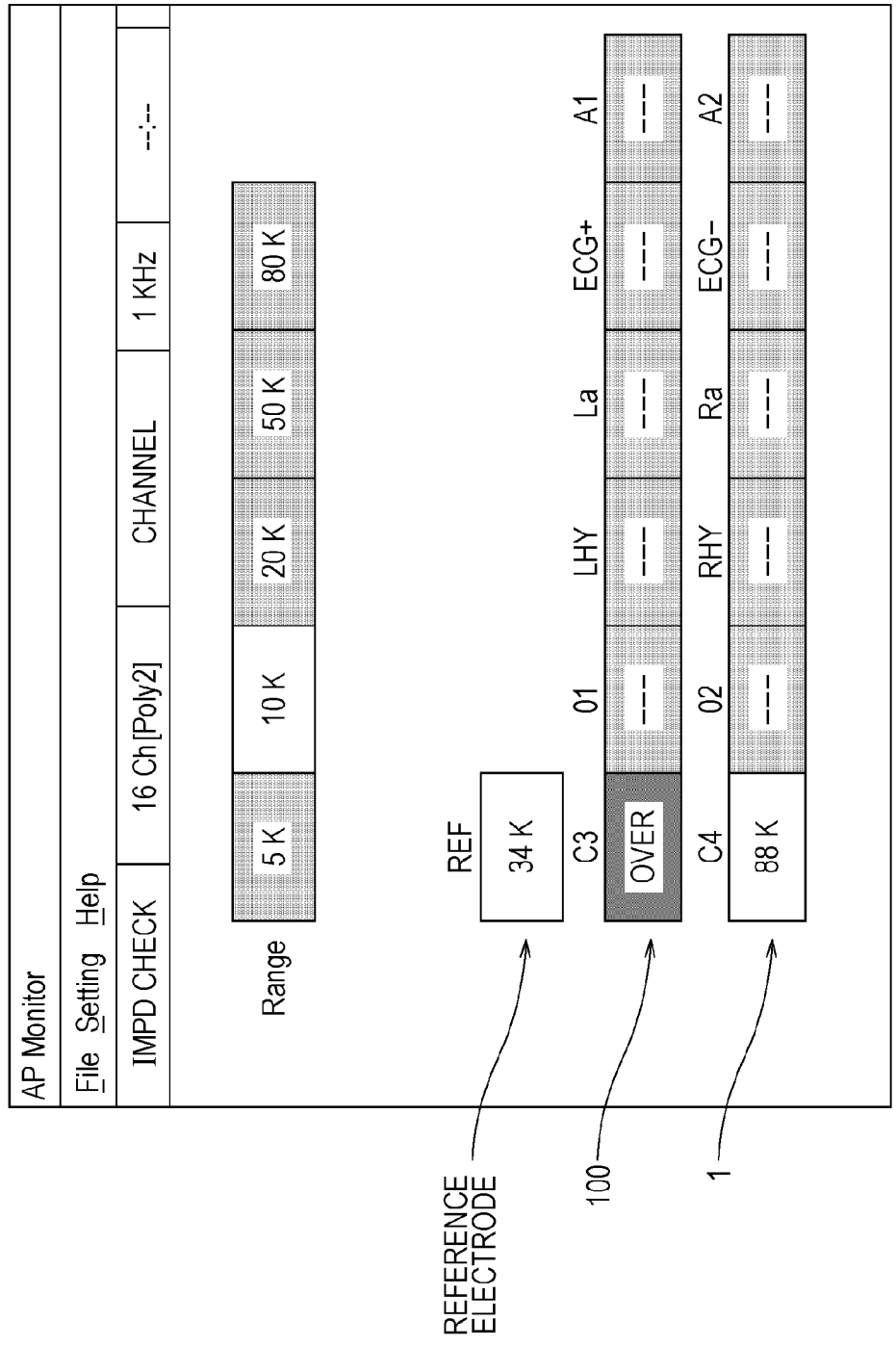
FIG. 6 is a schematic diagram showing the measurement result of impedances.

The measurement results are shown in FIG. 6. When impedances are measured, a medical standard of 10 kΩ was set as the range. As a result of the measurement, the impedance of the reference electrode was 34 kΩ, the impedance of the coil electrode 100 exceeded 100 kΩ, and the impedance of the electrode 1 was 88 kΩ, which falls within the allowable range of measurement of brain waves. Accordingly, the electrode 1 has an impedance large enough to measure brain waves.

As described above, since horny layers easily develop in the scalp because much sebum cutaneum is secreted and metabolism is rapid, measurement of brain waves is difficult in the case of a dry electrode such as the coil electrode 100, which has a large impedance. On the other hand, since the electrode 1 is a wet electrode that has the drought-resistant electrolytic solution soaking part 3 soaked in a drought-resistant electrolytic solution, brain waves can be measured even if horny layers easily develop because much sebum cutaneum is secreted.

Figure 7:
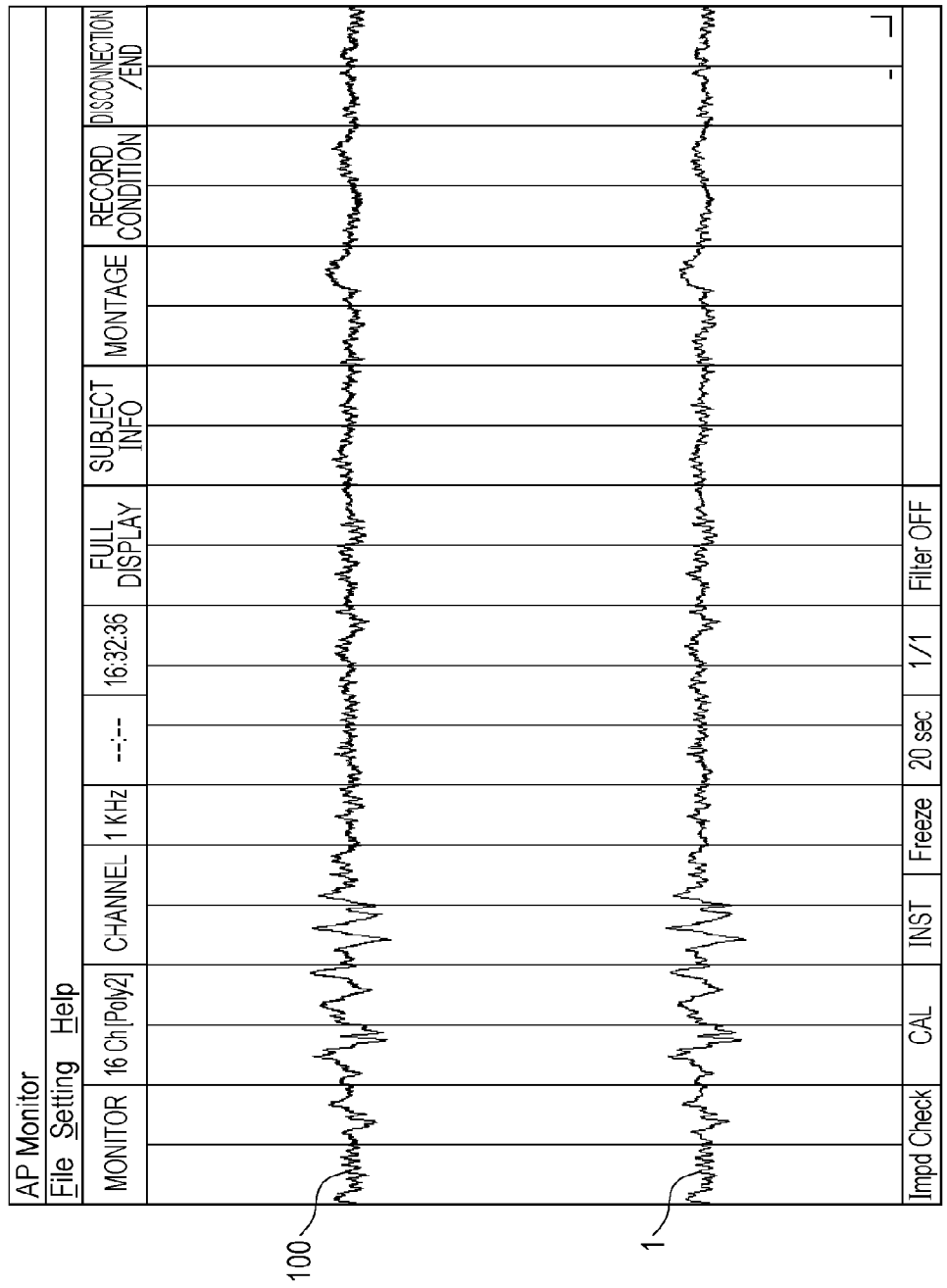
FIG. 7 is a schematic diagram showing the measurement result of brain waves.

FIG. 7 shows the brain waves measured by the electrode 1 and the coil electrode 100 that were placed at the vertex when the reference electrode is placed at the ear lobule. As is clear from FIG. 7, the electrode 1 and the coil electrode 100 measure brain waves having almost the same amplitude. Accordingly, the electrode 1 measures brain waves as accurately as the commercially available electrode.

3. Entire Configuration of a Biological Signal Detection Apparatus

Figure 8:
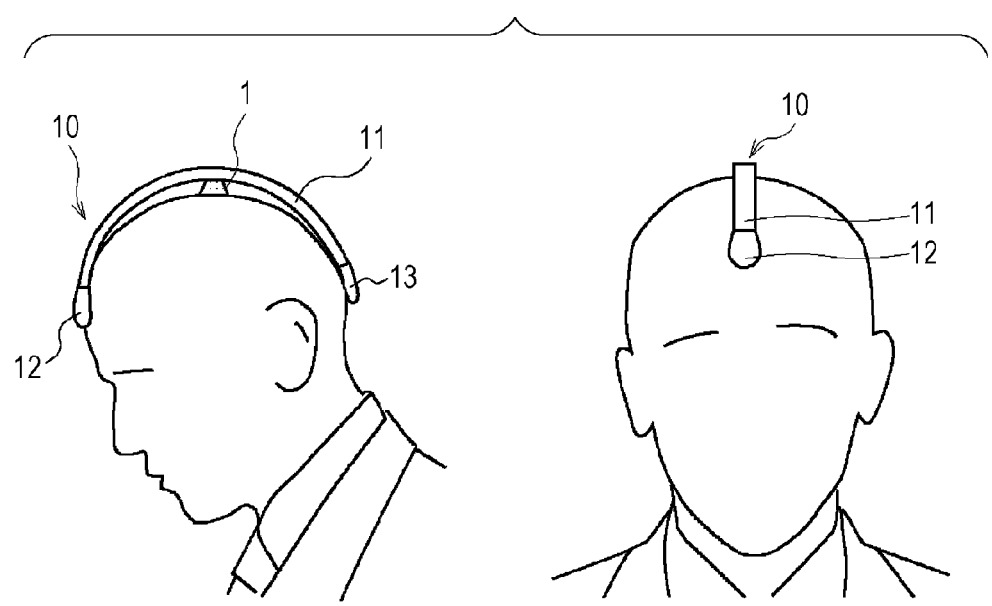
FIG. 8 is a schematic diagram showing the configuration and wear state of a biological signal detection apparatus.

FIG. 8 shows the entire configuration of a biological signal detection apparatus 10 having the electrode 1. The biological signal detection apparatus 10 has a support body 11 (also referred to as the hair band 11) that holds a head. The hair band 11 is an elastic plastic or metal plate that is formed in a "C" shape.

The hair band 11 has the electrode 1 attached to a predetermined position (facing the vertex of the wearer wearing the hair band) on the inner surface of a "C" shape bend.

Non-slip pads 12 and 13 made of rubber or other materials are disposed on one end and the other end of the hair band 11, respectively. The ends of non-slip pads 12 and 13 are curved so as to prevent the ends from jamming into the head.

The biological signal detection apparatus 10 are supported by the non-slip pads 12 and 13 and the electrode 1, which make contact with the wearer, and the biological signal detection apparatus 10 generates a pushing force that pushes the electrode 1 against the wearer's scalp.

Accordingly, in the biological signal detection apparatus 10, the end 3A of drought-resistant electrolytic solution soaking part 3 is kept in contact with the wearer's scalp.

4. Circuit Configuration of the Biological Signal Detection Apparatus

FIG. 9 shows the configuration of a signal processing unit 20 disposed in a predetermined position of the biological signal detection apparatus 10. The signal processing unit 20 includes a differential amplifier 31, a filter 32, an A/D (analog/digital) converter 33, an analyzer 34, a memory 35, and a communication unit 36.

The differential amplifier 31 amplifies the potential difference between the electrode 1 and the reference electrode (not shown) placed at, for example, the wearer's ear lobule as brain wave signals and gives the amplified biological signal to the filter 32.

The target frequency band is set for the filter 32. The filter 32 removes the signal components not included in the set target frequency band and gives the brain wave signals from which the signal components not included in the set target frequency band have been removed to the A/D converter 33.

In this embodiment, the target frequency band corresponds to the brain wave and the brain wave signals from which the signal components not included in the set target frequency band have been removed are given to the A/D converter 33.

The frequency bands that correspond to the brain wave include the delta waves (1 to 3 Hz), theta waves (4 to 7 Hz), alpha waves (8 to 13 Hz), beta waves (14 to 30 Hz), gamma waves (31 to 64 Hz), omega waves (65 to 128 Hz), rho waves (129 to 512 Hz), and sigma waves (513 to 1024 Hz). Some or all of these waves are set so as to be changeable by a predetermined operation unit as the target frequency bands.

The A/D converter 33 converts the brain wave signals into digital data (also referred to below as brain wave data) and gives the digital data to the analyzer 34.

The analyzer 34 includes a CPU (central processing unit), a ROM (read only memory), and RAM (random access memory), which is work memory for the CPU. The ROM stores a program etc. used to perform analysis.

When receiving a command for starting measurement, the analyzer 34 loads a program stored in the ROM into the RAM and performs various processes according to the program. The analyzer 34 also stores brain wave data given by the A/D converter 33 in the memory 35.

The analyzer 34 determines the stage of non-REM sleep or REM sleep based on the brain wave data given by the A/D converter 33, and associates the determination results with the brain wave data.

The stage is determined on the basis of elements such as the rate of appearance of delta waves, theta waves, or alpha waves per unit time and the time period for which a predetermined rate of appearance is kept.

The communication unit 36 uses, for example, wireless communication to transmit, to a predetermined external device, brain wave data given by the analyzer 34 or brain wave data stored in the memory 35 according to the command from the operation unit.

5. Operation and Effects

In the above configuration, the electrode 1 has a plurality of drought-resistant electrolytic solution soaking parts 3 that are formed so as to have a thickness (for example, 2 mm) allowing contact with the scalp without sandwiching hair connected to the conductive electrode element 2. The drought-resistant electrolytic solution soaking parts 3 are soaked in a drought-resistant electrolytic solution including a water-retentive (drought-resistant) liquid (glycerin) and a conductive liquid (physiological saline).

Accordingly, in the electrode 1, when the ends 3A make contact with the scalp 50 of the test subject, brain wave signals can be transferred to the electrode element 2 through the drought-resistant electrolytic solution soaking parts 3. At this time, the electrode 1 has an impedance large enough to measure the brain wave signals accurately, as described above.

Also, since the electrode 1 has the drought-resistant including electrolytic solution (glycerin) for preventing the conductive liquid (physiological saline) from evaporating, it is possible to stably measure brain waves even for a long period of time.

In addition, the electrode 1 has a hole into which the plurality of drought-resistant electrolytic solution soaking parts 3 are inserted and the support part 4, which is shrinkable and has the bottom 4A that makes contact with the scalp 50 and is sufficiently larger than the end surfaces of the plurality of drought-resistant electrolytic solution soaking parts 3.

Accordingly, since the bottom surface 4A, which has a larger area, of the support part 4 makes contact with the scalp 50 or the hair 51 in the electrode 1 when the ends 3A of the drought-resistant electrolytic solution soaking parts 3 make contact with the scalp 50, the state where the ends 3A make contact with the scalp 50 is kept more stable.

In the electrode 1, even when the hair 51 of the test subject is present, the support part 4 shrinks in the height direction by the thickness of the hair 51 sandwiched between the bottom surface 4A of the support part 4 and the scalp 50. Accordingly, the electrode 1 pushes the hair 51 against the scalp 50 by a restoring force and the state where the ends 3A make contact with the scalp 50 is kept more stable.

Since the drought-resistant electrolytic solution soaking part 3 is closely inserted into the through hole of the support part 4 so that almost all parts are covered, drying of the drought-resistant electrolytic solution in the drought-resistant electrolytic solution soaking parts 3 is suppressed, thereby enabling measurement for a longer period of time.

In the above configuration, the drought-resistant electrolytic solution soaking parts 3 that are formed to have a thickness that allows contact with the scalp by pushing through hair and are soaked in the drought-resistant electrolytic solution are connected to the electrode element 2. Since this enables the ends 3A of the drought-resistant electrolytic solution soaking parts 3 to easily make contact with the scalp 50 and the evaporation of the conductive liquid to be suppressed, measurement of brain waves can be performed stably for a long time.

2. Other Embodiments

The drought-resistant electrolytic solution soaking part 3 created by winding the textile piece 3C around the core 3B is used in the above embodiment, but the present application is not limited to this example and another drought-resistant electrolytic solution soaking part with a different shape may be used.

Figure 10A:
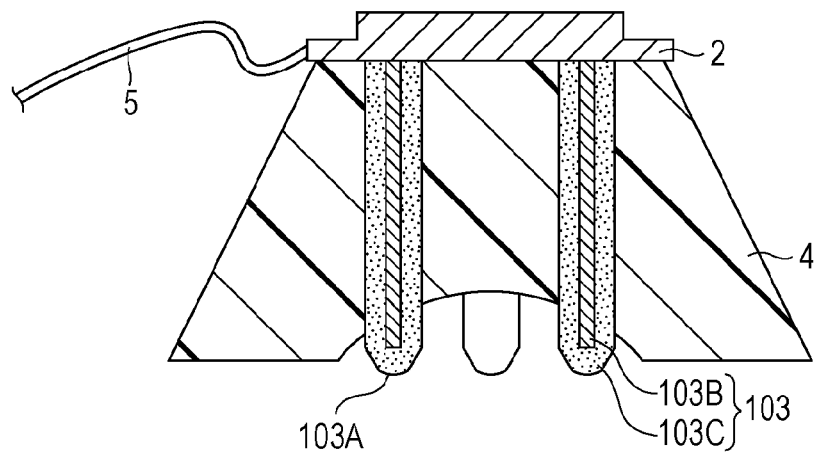
FIGS. 10A, 10B, and 10C are schematic diagrams showing electrodes according to other embodiments.

In another embodiment shown in FIG. 10A, a drought-resistant electrolytic solution soaking part 103 of the electrode 100 is formed in a substantially circular shape as a whole, a textile piece 103C is wound around a core 103B, and an end 103C is formed in a substantially conical shape with a round vertex.

Figure 10B:
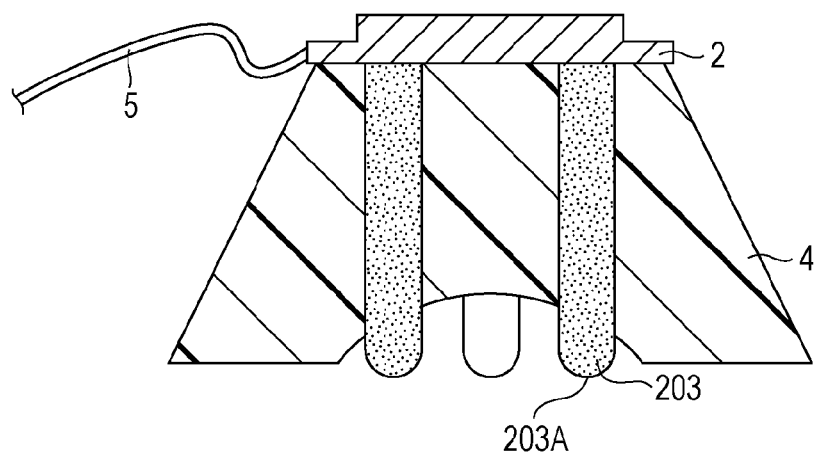

In still another embodiment shown in FIG. 10B, a drought-resistant electrolytic solution soaking part 203 of an electrode 200 is formed in a substantially circular shaped as a whole and includes a compressed felt bar whose end 203A is substantially hemispherical. Since the drought-resistant electrolytic solution soaking part 203 including the compressed felt bar stores a drought-resistant electrolytic solution by a capillary phenomenon and, when the scalp 50 makes contact with the end 203A, it transfers brain wave signals to the electrode element 2. The drought-resistant electrolytic solution soaking part 203 including the compressed felt bar also has a strength that prevents a bend when it makes contact with the scalp 50.

Figure 10C:
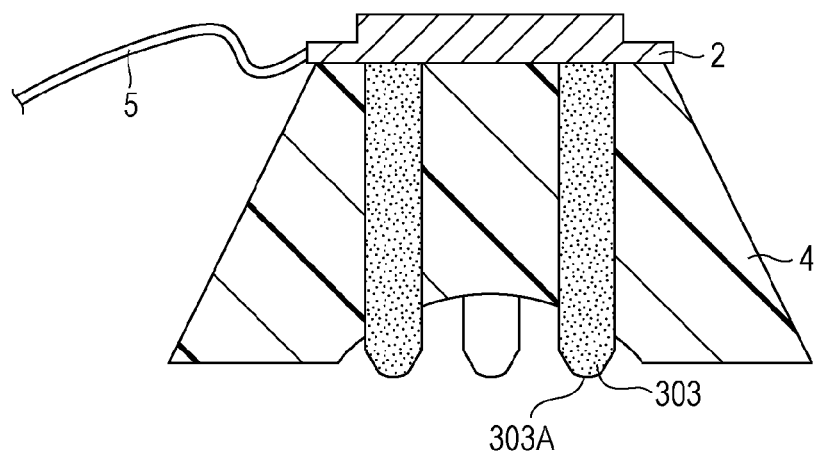

In yet another embodiment in FIG. 10C, a drought-resistant electrolytic solution soaking part 303 of an electrode 300 is formed in a substantially circular shape as a whole, and includes a compressed felt bar whose end 303A is substantially conical.

As described above, the material applicable to the drought-resistant electrolytic solution soaking part is the one that stores a drought-resistant electrolytic solution internally and has a strength that prevents a bend when the drought-resistant electrolytic solution soaking part makes contact with the scalp.

In the embodiment described first, the diameter of the drought-resistant electrolytic solution soaking part 3 is 2 mm, but the present application is not limited to this example and a diameter of approximately 2 mm or less may be applicable, which allows the drought-resistant electrolytic solution soaking part 303 to reach the scalp without the hair being sandwiched therebetween.

In the embodiment described first, the drought-resistant electrolytic solution with a mixing ratio (between physiological saline and glycerin) of 3:7 is used. The present application is not limited to this example and a drought-resistant electrolytic solution with a mixing ratio (between physiological saline and glycerin) of 1:1 may be used as long as the conductivity and water-retention are ensured.

In the embodiment described first, glycerin is added to prevent evaporation of physiological saline in the drought-resistant electrolytic solution. The present application is not limited to this example and a drought-resistant electrolytic solution containing physiological saline and another water-retentive substance such as hyaluronic acid or collagen may be used to prevent evaporation of physiological saline.

In the embodiment described first, physiological saline is used to add conductivity to the drought-resistant electrolytic solution. The present application is not limited to this example and another conductive solution such as a potassium chloride solution may be used.

In the embodiment described first, the support part 4 is formed in a substantially truncated-conical shape. The present application is not limited to this example and the support part 4 may be formed in a substantially cylindrical shape whose upper and bottom surfaces have substantially the same area as in the electrode element 2.

In the embodiment described first, the support part 4 is soaked in nothing. The present application is not limited to this example and the support part 4 may be soaked in the drought-resistant electrolytic solution. In this case, since the support part 4 makes contact with the drought-resistant electrolytic solution soaking part 3 in the electrode 1, the drought-resistant electrolytic solution flows from the support part 4 to the drought-resistant electrolytic solution soaking part 3 to enable measurement for a longer period of time.

In the embodiment described first, the biological signal detection apparatus 10 is used to bring the electrode 1 into contact with the scalp of the test subject. The present application is not limited to this example and a predetermined holding unit such as a headgear may be used to bring the electrode 1 into contact with the scalp of the test subject. That is, any holding unit that generates a pushing force for pushing the electrode 1 against the scalp of the test subject may be used.

In the embodiment described first, the drought-resistant electrolytic solution soaking part 3 receives the drought-resistant electrolytic solution only through a soak. The present application is not limited to this example and a container for storing the drought-resistant electrolytic solution may be disposed on the side of the electrode element 2 opposite to the drought-resistant electrolytic solution soaking part 3 and a textile member is used to connect the container to the drought-resistant electrolytic solution soaking part 3.

In the embodiment described first, the electrode element 2 is disposed as an electrode element and the drought-resistant electrolytic solution soaking part 3 is disposed as a drought-resistant electrolytic solution soaking part. The present application is not limited to this example and other electrode elements and drought-resistant electrolytic solution soaking parts with different configurations may be disposed.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A biological signal detection electrode comprising:
   an electrode element that is made of a conductive material and has a surface;
   a plurality of drought-resistant electrolytic solution soaking parts that are placed at predetermined intervals on the surface of the electrode element, are formed to have a thickness that allows contact with a scalp without hair being sandwiched between the electrode element and the scalp, and are soaked in a drought-resistant electrolytic solution including a drought-resistant liquid and a conductive liquid; and
   a support part that is formed to have an almost the same height as the plurality of drought-resistant electrolytic solution soaking parts, has through holes on a surface with an area larger than areas of the plurality of drought-resistant electrolytic solution soaking parts, into which the plurality of drought-resistant electrolytic solution soaking parts are inserted, and shrinks by the thickness of the hair sandwiched between the plurality of drought-resistant electrolytic solution soaking parts and the scalp of the test subject when ends of the plurality of drought-resistant electrolytic solution soaking parts opposite to a side of the electrode element are pushed against the scalp of the test subject with a predetermined pushing force in the state where the plurality of drought-resistant electrolytic solution soaking parts are inserted into the through holes.

2. The biological signal detection electrode of claim 1, wherein the drought-resistant electrolytic solution includes conductive physiological saline and glycerin.

3. The biological signal detection electrode of claim 1, wherein the support part makes contact with the plurality of drought-resistant electrolytic solution soaking parts in the state where the plurality of drought-resistant electrolytic solution soaking parts are soaked in the drought-resistant electrolytic solution and are inserted into the through holes.

4. The biological signal detection electrode of claim 1, wherein the support part has a surface facing the electrode element and a surface opposite to the surface facing the electrode element, the surface opposite to the surface facing the electrode element being larger than the surface facing the electrode element.

5. The biological signal detection electrode of claim 1, wherein any adjacent pair of the plurality of drought-resistant electrolytic solution soaking parts is spaced apart by the distance larger than the diameter of the plurality of drought-resistant electrolytic solution soaking parts.

6. A biological signal detection apparatus comprising:
   an electrode that has an electrode element made of a conductive material, the electrode element having a surface, and a plurality of drought-resistant electrolytic solution soaking parts that are placed at predetermined intervals on the surface of the electrode element, are formed to have a thickness allowing contact with a scalp without hair being sandwiched between the electrode element and the scalp, and are soaked in a drought-resistant electrolytic solution including a drought-resistant liquid and a conductive liquid;
   a support part that is formed to have an almost the same height as the plurality of drought-resistant electrolytic solution soaking parts, has through holes on a surface with an area larger than areas of the plurality of drought-resistant electrolytic solution soaking parts, into which the plurality of drought-resistant electrolytic solution soaking parts are inserted, and shrinks by the thickness of the hair sandwiched between the plurality of drought-resistant electrolytic solution soaking parts and the scalp of the test subject when ends of the plurality of drought-resistant electrolytic solution soaking parts opposite to a side of the electrode element are pushed against the scalp of the test subject with a predetermined pushing force in the state where the plurality of drought-resistant electrolytic solution soaking parts are inserted into the through holes; and
   a pushing unit pushing the electrode with a predetermined pushing force against the scalp of a wearer.

* * * * *